United States Patent [19]

Segnitz et al.

[11] Patent Number: 4,784,843

[45] Date of Patent: Nov. 15, 1988

[54] DICYCLOHEXYLALKANES, THEIR PREPARATION, COSMETIC AND PHARMACEUTICAL FORMULATIONS CONTAINING THESE COMPOUNDS, AND THEIR USE AS OIL COMPONENTS

[75] Inventors: Adolph Segnitz, Ibbenbueren; Knut Oppenlaender, Ludwigshafen; Paul Naegele, Neuhofen, all of Fed. Rep. of Germany

[73] Assignee: BASF Aktiengesellschaft, Rheinland-Pfalz, Fed. Rep. of Germany

[21] Appl. No.: 831,451

[22] Filed: Feb. 20, 1986

[30] Foreign Application Priority Data

Mar. 1, 1985 [DE] Fed. Rep. of Germany ....... 3507175

[51] Int. Cl.$^4$ ........................ A61K 7/021; A61K 7/06; A61K 7/42
[52] U.S. Cl. ......................................... 424/63; 424/59; 424/70; 585/10; 585/20; 514/844
[58] Field of Search ............... 514/789, 844, 845, 846, 514/847, 848; 424/70, 59, 63; 585/10, 20

[56] References Cited

U.S. PATENT DOCUMENTS 3,886,287  5/1975  Kobayashi et al. ................ 514/789
4,457,944  7/1984  Conrad et al. .................... 585/20 X
4,556,503  12/1985  Tsubouchi et al. .
4,593,048  6/1986  Sato et al. ...................... 514/789 X

FOREIGN PATENT DOCUMENTS 0135871  4/1985  European Pat. Off. .

OTHER PUBLICATIONS

Petrov, A. D. et al., Zhur. Obshchei Khum, 30, "Synthesis of Diphenulalkine", pp. 2838-2846 (1960).
Teterina, M. P. et al., Neftekhimiya 3(4) "Strentching Vibrations of C—H Bond of Hydrocarbons", pp. 451-455 (1963).
Angewandte Chemie, vol. 89, No. 12, 1977, pp. 913-914.
Angewandte Chemie, Int. Ed. Engl., vol. 16, 1977, No. 12, pp. 875 and 876.

Primary Examiner—John F. Terapane
Assistant Examiner—John S. Maples
Attorney, Agent, or Firm—Oblon, Fisher, Spivak, McClelland & Maier

[57] ABSTRACT

Dicyclohexylalkanes, their preparation, cosmetic and pharmaceutical formulations containing these compounds, and their use in these formulations as oil components for cosmetic and pharmaceutical purposes.

9 Claims, No Drawings

DICYCLOHEXYLALKANES, THEIR PREPARATION, COSMETIC AND PHARMACEUTICAL FORMULATIONS CONTAINING THESE COMPOUNDS, AND THEIR USE AS OIL COMPONENTS

The present invention relates to dicyclohexylalkanes, their preparation, cosmetic and pharmaceutical formulations containing these compounds, and their use as oil components for cosmetic and pharmaceutical purposes.

In the preparation of, in particular, cosmetic or pharmaceutical formulations for a very wide variety of specific purposes, there is a great demand for medical white oils or liquid paraffins. Furthermore, a substitute for liquid paraffin has long been sought. When applied externally to the skin, liquid paraffin has the disadvantage of certain occlusive action and is therefore avoided as far as possible in formulations for external application. For example, European Patent Application No. 72,988 describes the use of 1,3-dialkylcyclohexane compounds as cosmetic oils.

It is an object of the present invention to provide novel oils to replace liquid paraffins for cosmetic and pharmaceutical purposes.

We have found that this object is achieved, and that dicyclohexylalkanes of the formula I

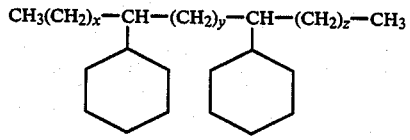

where x, y and z are each from 0 to 24, preferably from 0 to 14, and the sum $x+y+z$ is from 4 to 24, preferably from 4 to 14, are very useful as oil components in cosmetic and pharmaceutical formulations.

Depending on the meanings of x, y and z, the compounds of the formula I possess linear alkyl chains containing a total of 8 to 28, preferably 8 to 18, carbon atoms. As a consequence of the preparation, the cyclohexyl radicals are randomly distributed in the chain on secondary carbon atoms, preferably on the carbon atoms adjacent to the terminal methyl groups. As a rule, the preparation excludes the possibility of geminal cyclohexyl groups.

The dicyclohexylalkanes of the formula I are prepared by hydrogenating the parent diphenylalkanes (compounds of the formula I which contain benzene radicals) with hydrogen under from 90 to 220 bar and at from 150° to 350° C. in the presence of a hydrogenation catalyst.

As a rule, the starting compounds are not pure compounds but industrial mixtures of diphenylalkanes having chain lengths of, in particular, 10-14, 13 and 14, 9-15 and 10-18 carbon atoms. A chain length of from 10 to 14 carbon atoms is preferred.

The diphenylalkanes used as starting compounds can be obtained in a conventional manner by thermal chlorination or photochlorination of the corresponding paraffin hydrocarbons. The resulting chloroparaffin mixtures are reacted with benzene in the presence of AlCl$_3$. The dichloroalkanes react in a known manner to give diphenylalkanes. In this reaction, the phenyl radicals are introduced into the chain preferentially at the secondary carbon atoms. Because of the different boiling ranges, the diphenylalkanes can be readily separated from mono- and polyphenylalkanes by distillation (H.-D. Wulf et al., Fette, Seife, Anstrichmittel, 69 (1967), 32 et seq.).

The diphenylalkanes obtained in the industrial production of straight-chain alkylbenzenes are advantageous starting materials.

The diphenylalkanes or the industrial mixtures are hydrogenated under the stated conditions.

The hydrogenation can be carried out continuously or batchwise in a single-stage or two-stage procedure.

Advantageous hydrogenation catalysts are catalysts based on noble metals, in particular palladium or platinum, on a conventional carrier, such as alumina or silica, or those based on nickel and/or nickel-molybdenum.

The preferred catalysts are Raney nickel, in particular for the single-stage hydrogenation, nickel-molybdenum on magnesium silicate and/or molybdenum-nickel on alumina, the latter for the two-stage hydrogenation, as described in the Example.

For example, measurement of the UV absorption can be used to determine when hydrogenation is complete.

The dicyclohexylalkanes are obtained as colorless and odorless oils having an extremely low extinction of of 0.01 at 275 nm, according to DAB 8 (German Pharmacopoeia, 8th edition). Such outstanding extinction values are not usually achieved by liquid paraffins. The rating in the sulfuric acid test according to DAB 8 is excellent, at <1.

They are very useful as oil components in pharmaceutical and cosmetic formulations, in particular for external purposes but also for internal formulations. They are very well tolerated and possess good spreading properties on the skin, which could not be foreseen. Consequently, the moisture permeability of the skin is not disturbed, and the hot feeling frequently produced by ointment bases on the skin as a result of the covering properties is avoided. The novel oils are very readily emulsifiable so that in practical use it is frequently possible to manage with less than the usual amount of emulsifier. There are outstanding solvents for a large number of oil-soluble ingredients, such as sunscreen agents, vitamins or ethereal oils and perfumes.

The present invention accordingly also relates to formulations for cosmetic or pharmaceutical purposes which contain dicyclohexylalkanes of the formula I as oil components, in addition to conventional constituents, assistants and, where relevant, active compounds, and to the use of the dicyclohexylalkanes of the formula I as oil components in cosmetic and pharmaceutical formulations.

Examples of advantageous formulations, in particular in the form of oil-in-water or water-in-oil emulsions or in the form of conventional ointments, are the very wide variety of creams, such as skin creams, nutrient creams, moisturizing creams, baby creams, sport creams and sunscreen creams.

Suspensions, gels and lotions are also suitable formulations.

Other examples of formulations are those for hair care, such as hair conditioners, hair sprays, etc.

The novel dicyclohexylalkanes can also successfully be used in skin-care oils, sunscreen oils, massage oils, bath oils or oils for children.

The dicyclohexylalkanes may be present in the novel formulations in amounts of from 0.1 to 95, preferably from 0.1 to 60, % by weight.

For the formulations, which are generally in the form of emulsions, suspensions or ointments, from 3 to 30, preferably from 6 to 20, % by weight are suitable. Skin-care oils advantageously contain from 10 to 95, preferably from 30 to 60, % by weight. Because of their plasticizing and gloss-imparting properties, small amounts of from 0.1 to 3.0% by weight are preferably used in hair-care formulations.

In the very side variety of formulations, the dicyclohexylalkanes used according to the invention can be readily processed together with the very wide range of conventional carriers and diluents, assistants and, where relevant, active compounds.

Examples of advantageous conventional components of cosmetic and pharmaceutical formulations are anionic, cationic and non-ionic emulsifiers and emulsion stabilizers, which may simultaneously impart consistency or be gel formers, eg. polyvinylpyrrolidone, fatty alcohols, glycerol monostearate, polyacrylic acids, cellulose derivatives and ethylene oxide/propylene oxide block polymers, solid or liquid oil components or fatty substances of mineral, vegetable or animal origin, synthetic ester oils, such as triglyceride esters and isopropyl myristate, and hydrophilic components, such as glycerol, polyethylene glycol and propylene glycol.

Other examples of ingredients are sunscreen agents, tanning agents, preservatives, antioxidants, pigments, dyes, ethereal oils and perfume oils, vitamins, plant extracts, collagen, etc. These substances are described in, for example, CTFA, Cosmetic Ingredient Dictionary, 3rd edition, Washington 1982.

Examples of specific pharmaceutical formulations are zinc ointments, rheumatic ointments, bronchial ointments or creams containing hydrocortisone acetate, as described in the Examples.

The Examples which follow illustrate the invention.

Preparation of dicyclohexylalkanes

1. Single-stage process

Diphenylalkanes having chain lengths of from 10 to 14 carbon atoms are hydrogenated in an autoclave in the presence of Raney nickel under a hydrogen pressure of 200 bar and at 280° C. for 100 hours. 689 l (S.T.P.) of $H_2$ are consumed per liter of diphenylalkane employed. The extinction of the resulting dicyclohexylalkane at 260 nm is 0.12 cm$^{-1}$.

2. Two-stage hydrogenation (a) Diphenylalkane having chain lengths of from 10 to 14 carbon atoms are hydrogenated continuously under a hydrogen pressure of 95 bar and at 350° C. in the presence of a molybdenum-nickel catalyst on alumina, at a throughput of 900 g/hour. 250 l/hour of hydrogen are absorbed.

The resulting mixture has an extinction of about 200 cm$^{-1}$ at 275 nm.

(b) Compete hydrogenation is carried out in the presence of a nickel-molybdenum catalyst on magnesium silicate under a hydrogen pressure of 205 bar and at 180° C., at a throughput of 600 g/hour. 240 l/hour of hydrogen are absorbed.

The properties of the resulting dicyclohexylalkane are given in the Table below:

|  | After the 1st stage | After the 2nd stage |  |
|---|---|---|---|
| Color: | colorless | transparent |  |
| Density at 15° C.: | 0.891 | 0.877 | g/cm$^3$ |
| Viscosity at 40° C.: | 21.67 | 27.22 | mm$^2$/s |
| Viscosity at 50° C.: | 14.62 | 17.91 | mm$^2$/s* |
| Viscosity at 100° C. | 3.80 | 4.36 | mm$^2$/s |
| Viscosity index: | 28 | 37 |  |
| Flashpoint COC: | 204° C. | 204 | °C. |
| $n_D20$: | 1.4921 | 1.4789 |  |
| Pour point: | <−50° C. | −49 | °C. |
| UV 275 nm: | about 200 | 0.01 | cm$^{-1}$ |
| 295 nm: | — | 0.01 | cm$^{-1}$ |
| 300 nm: | — | 0.01 | cm$^{-1}$ |
| $H_2SO_4$ rating: | — | <1 |  |
| Acid number | — | 0 |  |

*corresponds to 2.64° Engler

EXAMPLES OF USE

General formulations containing $C_{10}/C_{14}$ dicyclohexylalkanes. Parts are by weight.

| Nutrient cream (O/W type) | |
|---|---|
| $C_{16}/C_{18}$-fatty alcohol with 6 moles of EO (ethylene oxide) | 2.0 |
| $C_{16}/C_{18}$-fatty alcohol with 25 moles of EO | 2.0 |
| Oil component according to the invention | 15.0 |
| Cetyl alcohol | 2.0 |
| Glycerol monostearate | 6.0 |
| Peanut oil | 5.0 |
| Vitamin oil | 1.0 |
| Silicone oil 100 | 0.1 |
| 1,2-Propylene glycol | 3.0 |
| Preservative | 0.5 |
| Perfume oil | 0.2 |
| Water | 63.2 |
| Moisturizing cream (O/W type) | |
| $C_{16}/C_{18}$-fatty alcohol with 6 moles of EO | 1.5 |
| $C_{16}/C_{18}$-fatty alcohol with 25 moles of EO | 1.5 |
| Oil component according to the invention | 6.0 |
| $C_{16}/C_{18}$ ester of ethylhexanoic acid | 6.0 |
| Cetyl stearyl alcohol | 7.0 |
| 1,2-Propylene glycol | 3.0 |
| Humectant | 2.0 |
| Preservative | 0.5 |
| Perfume oil | 0.2 |
| Water | 72.3 |
| Baby cream (O/W type) | |
| $C_{16}/C_{18}$-fatty alcohol with 6 moles of EO | 2.0 |
| $C_{16}/C_{18}$-fatty alcohol with 25 moles of EO | 2.0 |
| $C_{16}/C_{18}$ ester of ethylhexanoic acid | 5.0 |
| Oil component according to the invention | 5.0 |
| Cetyl alcohol | 4.0 |
| Glycerol monostearate | 4.0 |
| (±)-α-Bisabolol | 0.3 |
| Allantoin | 0.2 |
| 1,2-Propylene glycol | 5.0 |
| Preservative | 0.5 |
| Perfume oil | 0.2 |
| Water | 71.8 |
| Handcream (O/W type) | |
| $C_{16}/C_{18}$-fatty alcohol with 6 moles of EO | 2.0 |
| $C_{16}/C_{18}$-fatty alcohol with 25 moles of EO | 2.0 |
| Oil component according to the invention | 9.0 |
| Cetyl alcohol | 5.0 |
| Glycerol monostearate | 5.0 |
| Silicone oil 350 | 1.0 |
| Polyvinylpyrrolidone, K value 30 | 1.0 |
| Glycerol | 10.0 |
| Preservative | 0.5 |
| Perfume oil | 0.2 |
| Water | 64.3 |
| Sport cream (W/O type) | |
| Hydrogenated castor oil with 7 moles of EO | 3.0 |
| $C_{16}/C_{18}$ ester of ethylhexanoic acid | 10.0 |
| Oil component according to the invention | 10.0 |
| Microcrystalline wax | 8.0 |
| Lanoline alcohol | 1.0 |
| 1,2-Propylene glycol | 3.0 |

| -continued | |
|---|---|
| Preservative | 0.5 |
| Perfume oil | 0.3 |
| Water | 64.2 |
| Hair conditioner | |
| C$_{16}$/C$_{18}$-fatty alcohol with 6 moles of EO | 1.5 |
| C$_{16}$/C$_{18}$-fatty alcohol with 25 moles of EO | 1.5 |
| Cetyl stearyl alcohol | 3.0 |
| Oil component according to the invention | 3.0 |
| 1,2-Propylene glycol | 2.0 |
| Copolymer of vinylpyrrolidone and vinylimidazoline methochloride | 3.0 |
| Citric acid | 0.5 |
| Preservative | 0.5 |
| Perfume oil | 0.2 |
| Water | 81.8 |
| Hairspray | |
| Film former | 2.5 |
| Ethanol | 20.0 |
| Methylene chloride | 25.0 |
| Oil component according to the invention | 0.2 |
| Propellants | 52.3 |
| Care lotion (after sun, O/W type) | |
| C$_{16}$/C$_{18}$-fatty alcohol with 6 moles of EO | 2.0 |
| C$_{16}$/C$_{18}$-fatty alcohol with 25 moles of EO | 2.0 |
| Oil component according to the invention | 15.0 |
| C$_{16}$/C$_{18}$ ester of ethylhexanoic acid | 7.0 |
| Oil component according to the invention | 8.0 |
| Cetyl alcohol | 1.0 |
| Glycerol monostearate | 6.0 |
| Silicone oil 100 | 0.1 |
| Panthenol | 1.0 |
| (±)-α-Bisabolol | 0.2 |
| 1,2-Propylene glycol | 3.0 |
| Preservative | 0.5 |
| Perfume oil | 0.2 |
| Water | 68.9 |
| Sunscreen oil | |
| Oil component according to the invention | 50.0 |
| C$_{16}$/C$_{18}$ ester of ethylhexanoic acid | 30.0 |
| Ethylhexyl p-methoxycinnamate | 3.0 |
| C$_{16}$/C$_{18}$-fatty alcohol with 25 moles of EO | 2.0 |
| Perfume oil | 0.3 |
| C$_8$–C$_{12}$-fatty acid triglyceride | 16.7 |
| Massage oil | |
| Oil component according to the invention | 60.0 |
| C$_{16}$/C$_{18}$ ester of ethylhexanoic acid | 40.0 |
| Bath oil | |
| Oil component according to the invention | 52.0 |
| Isopropyl myristate | 43.0 |
| Nonylphenol + 6 moles of EO | 5.0 |
| Body oils | |
| 1. Oil component according to the invention | 60.0 |
|    C$_{16}$/C$_{18}$ ester of ethylhexanoic acid | 20.0 |
|    C$_8$/C$_{12}$-fatty acid triglyceride | 20.0 |
| 2. Oil component according to the invention | 89.5 |
|    C$_{16}$/C$_{18}$ ester of ethylhexanoic acid | 10.0 |
|    (±)-α-bisabolol | 0.5 |
| Polyvinylpyrrolidone/iodine cream | |
| Micronized PVP/iodine | 10.0 |
| C$_{16}$/C$_{18}$-fatty alcohol with 6 moles of ethylene oxide | 2.0 |
| C$_{16}$/C$_{18}$-fatty alcohol with 25 moles of ethylene oxide | 2.0 |
| Oil component according to the invention | 10.0 |
| Cetyl stearyl alcohol | 10.0 |
| Glycerol | 5.0 |
| Water | 61.0 |
| Polyvinylpyrrolidone/iodine spray powder | |
| Micronized PVP/iodine | 4.4 |
| Oil component according to the invention | 1.5 |
| Silica | 1.0 |
| Fluorohydrocarbon propellant to make up to | 100.0 |
| Zinc ointment | |
| C$_{16}$/C$_{18}$-fatty alcohol with 25 moles of EO | 2.5 |
| Cetyl stearyl alcohol | 10.0 |
| Vaseline | 10.0 |
| Oil component according to the invention | 10.0 |
| Zinc oxide | 20.0 |
| Water | 47.5 |

| -continued | |
|---|---|
| Rheumatic ointment | |
| C$_{16}$/C$_{18}$-fatty alcohol with 8 moles of EO | 3.0 |
| C$_{16}$/C$_{18}$-fatty alcohol with 25 moles of EO | 3.0 |
| Glycerol monostearate | 10.0 |
| Vaseline | 20.0 |
| Oil component according to the invention | 10.0 |
| Pine needle oil | 3.0 |
| Rosemary oil | 2.0 |
| Methyl salicylate | 6.0 |
| Benzyl nicotinate | 1.5 |
| Water | 41.5 |
| Cream containing hydrocortisone acetate | |
| C$_{16}$/C$_{18}$-fatty alcohol with 6 moles of EO | 2.0 |
| C$_{16}$/C$_{18}$-fatty alcohol with 25 moles of EO | 2.0 |
| Cetyl alcohol | 4.0 |
| Glycerol monostearate | 4.0 |
| Oil component according to the invention | 10.0 |
| 1,2-Propylene glycol | 5.0 |
| Hydrocortisone acetate | 1.0 |
| Water | 72.0 |
| Bronchial ointment | |
| Stearic acid with 9 moles of EO | 10.0 |
| C$_{16}$/C$_{18}$-fatty alcohol with 25 moles of EO | 1.0 |
| Glycerol monostearate | 5.0 |
| Vaseline | 20.0 |
| Oil component according to the invention | 10.0 |
| Thyme oil | 1.0 |
| Sage oil | 1.0 |
| Rosemary oil | 2.0 |
| Eucalyptus oil | 1.0 |
| Terpentine oil | 4.0 |
| Dwarf pine needle oil | 2.0 |
| Menthol | 3.0 |
| Camphor | 6.0 |
| Water | 34.0 |
| Massage cream | |
| C$_{16}$/C$_{18}$-fatty alcohol with 6 moles of EO | 3.0 |
| C$_{16}$/C$_{18}$-fatty alcohol with 25 moles of EO | 1.1 |
| Cetyl stearyl alcohol | 6.0 |
| Oil component according to the invention | 30.0 |
| Paraffin, white, m.p. 50-55° C. | 5.0 |
| 1,2-Propylene glycol | 10.0 |
| Water | 44.9 |

We claim:

1. In a cosmetic or pharmaceutical formulation containing an oil component in combination with cosmetically or pharmaceutically acceptable ingredients, the improvement wherein the oil component contains a spreadably effective amount of a dicyclohexylalkane of the formula I

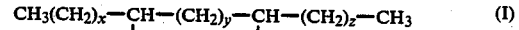
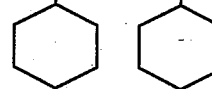

where x, y, and z are each from 0 to 24 and the sum x+y+z is from 4 to 24.

2. A formulation as claimed in claim 1, which contains from 0.1 to 95% by weight of a dicyclohexylalkane of the formula I.

3. A formulation according to claim 1 in which in the dicyclohexylalkane of the formula I, x, y and z are each from 0 to 14 and the sum x+y+z is from 4 to 14.

4. A formulation according to claim 1 in which in the dicyclohexylalkane of the formula I the alkyl chain contains a total of from 10 to 14 carbon atoms.

5. A formulation according to claim 2 in which there is a mixture of dicyclohexylalkanes in which the alkyl chain in formula (I) contains a total of 10 to 14 carbons and the cyclohexyl groups are randomly distributed in the chains on secondary carbon atoms thereof.

6. A formulation according to claim 5 in which the dicyclohexylalkane has an extinction coefficient of about 0.01 at 275 nm and a pour point about −49° C.

7. A formulation according to claim 6 containing 3 to 30 percent by weight of the dicyclohexylalkane, the balance being conventional cosmetic and/or pharmaceutical agents.

8. A formulation according to claim 6 which is a skin care oil containing 30 to 60 weight percent of the dicyclohexylalkanes, the balance being conventional skin care oil ingredients.

9. In a cosmetic hair care formulation which contains a film-former and an oil component, the improvement wherein the oil component contains a mixture of dicyclohexylalkanes of formula (I)

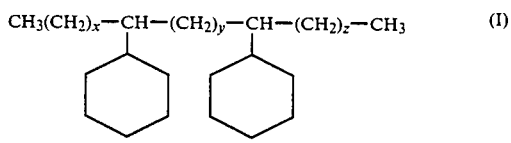

in which the alkyl chain in formula (I) contains a total of 10 to 14 carbons and the cyclohexyl groups are randomly distributed in the chains on secondary carbon atoms thereof, and in which x, y, and z may each be zero, provided that their sum is at least 6, the dicyclohexylalkane having an extinction coefficient of about 0.01 at 275 nm and a pour point of −49° C., the dicyclohexane being present in amount of 0.1 to 3.0% by weight of the total formulation.

* * * * *